United States Patent
Metzger

(10) Patent No.: US 9,254,074 B2
(45) Date of Patent: Feb. 9, 2016

(54) SELF-ADHESIVE CLEANING WIPE FOR DENTAL INSTRUMENTS

(71) Applicant: Rebecca J. Metzger, Ames, IA (US)

(72) Inventor: Rebecca J. Metzger, Ames, IA (US)

(*) Notice: Subject to any disclaimer, the term of this patent is extended or adjusted under 35 U.S.C. 154(b) by 0 days.

(21) Appl. No.: 14/176,495

(22) Filed: Feb. 10, 2014

(65) Prior Publication Data

US 2015/0223661 A1 Aug. 13, 2015

(51) Int. Cl.
| | |
|---|---|
| *A47L 25/00* | (2006.01) |
| *B08B 1/00* | (2006.01) |
| *A41D 19/00* | (2006.01) |
| *A61B 19/00* | (2006.01) |
| *A47L 13/16* | (2006.01) |
| *A47L 13/18* | (2006.01) |
| *A61C 19/00* | (2006.01) |

(52) U.S. Cl.
CPC .............. *A47L 25/00* (2013.01); *B08B 1/006* (2013.01); *A41D 19/0024* (2013.01); *A47L 13/16* (2013.01); *A47L 13/18* (2013.01); *A61B 19/34* (2013.01); *A61C 19/001* (2013.01); *A61C 19/002* (2013.01)

(58) Field of Classification Search
CPC ........ A61C 19/002; A61B 19/34; A61L 2/00; A61L 2/02; A61L 2/26; A61L 2202/17; B08B 1/001; B08B 1/003; B08B 1/006; A46B 5/04; A46B 9/005; A47L 13/00; A47L 13/10; A47L 13/16–13/19; A47L 25/00; A47L 23/00; A47L 23/20; A47L 23/22; A41D 19/00; A41D 19/0024; A41D 19/0055; A41D 13/08; A41D 13/081
USPC ........... 15/104.93, 104.94, 209.1, 210.1, 214, 15/227, 244.1, 244.3, 244.4, 215–217; 428/40.1, 41.7, 41.8; 2/16, 20, 21, 160, 2/161.1, 161.7, 161.8
See application file for complete search history.

(56) References Cited

U.S. PATENT DOCUMENTS

| | | | | |
|---|---|---|---|---|
| 2,763,885 | A * | 9/1956 | Lyons | 15/104.94 |
| 2,908,923 | A * | 10/1959 | Schlechter | 401/10 |
| 3,109,192 | A * | 11/1963 | Levenson | 15/210.1 |
| 3,412,418 | A * | 11/1968 | Griffin | 15/229.2 |
| 3,969,824 | A | 7/1976 | Widen et al. | |
| 3,985,383 | A * | 10/1976 | Yonkers | 294/25 |
| 4,353,944 | A * | 10/1982 | Tarui | 428/74 |
| 4,450,844 | A * | 5/1984 | Quisno | 600/556 |
| 4,593,427 | A * | 6/1986 | Ortolivo | 15/227 |
| 4,819,264 | A * | 4/1989 | Lemley | 379/452 |
| 4,822,669 | A * | 4/1989 | Roga | 442/373 |

(Continued)

FOREIGN PATENT DOCUMENTS

| | | | |
|---|---|---|---|
| DE | 19853252 | * | 3/2000 |
| JP | 1-164348 | * | 6/1989 |

OTHER PUBLICATIONS

Matrow, Robert and Elizabeth Ray; "Redesign of a dental mirror cleaning device;" A Major Qualifying Project Report; Apr. 26, 2010; pp. cover-37; Worcester Polytechnic Institute.

*Primary Examiner* — Mark Spisich
(74) *Attorney, Agent, or Firm* — Zarley Law Firm, P.L.C.

(57) ABSTRACT

A self-adhesive cleaning wipe for use in cleaning dental mirrors and instruments. The self-adhesive cleaning wipe is placed on the surface of protective gloves worn by dental professionals, thereby providing a conveniently accessible absorbent cleaning surface for mirrors and instruments when they become soiled, wet, or fogged. The self-adhesive cleaning wipe is removable and disposable in order to facilitate infection control.

14 Claims, 4 Drawing Sheets

(56) References Cited

U.S. PATENT DOCUMENTS

| | | | |
|---|---|---|---|
| 5,477,581 A * | 12/1995 | Wind | 15/210.1 |
| 5,654,824 A | 8/1997 | Tarr et al. | |
| 5,893,190 A * | 4/1999 | Mertz | 15/209.1 |
| 6,254,386 B1 | 7/2001 | Ohmes | |
| 6,280,529 B1 * | 8/2001 | Meyer | 134/6 |
| 6,458,442 B1 * | 10/2002 | McKay | 428/40.1 |
| 6,578,285 B2 * | 6/2003 | Turtzo | 34/89.1 |
| 7,325,675 B2 | 2/2008 | Halkyard | |
| 7,331,785 B2 | 2/2008 | Croop et al. | |
| 8,133,052 B1 | 3/2012 | Emmons, III | |
| 8,282,393 B2 | 10/2012 | Widen | |
| 8,584,298 B2 * | 11/2013 | Viscomi et al. | 15/104.92 |
| 2004/0026289 A1 * | 2/2004 | Halkyard | 206/494 |
| 2006/0000043 A1 * | 1/2006 | Jou-Chen et al. | 15/231 |
| 2006/0166170 A1 * | 7/2006 | Masters | 433/215 |
| 2007/0186355 A1 * | 8/2007 | Cancelmo et al. | 8/147 |
| 2007/0283515 A1 * | 12/2007 | Viscomi et al. | 15/104.94 |
| 2008/0028561 A1 * | 2/2008 | Ros | 15/230.11 |

* cited by examiner 2a  2b  2c 2d  2e

SELF-ADHESIVE CLEANING WIPE FOR DENTAL INSTRUMENTS

BACKGROUND OF THE INVENTION

This invention is directed toward a cleaning wipe. More particularly a self-adhesive cleaning wipe for dental instruments.

It is widely known that dentists use a small round mirror mounted at an angle at the end of an elongated shaft or handle. Dental mirrors are used by dentists and dental hygienists to view portions of the patient's mouth, teeth, and tissues that would otherwise be visually inaccessible. During dental procedures, the reflective surface of the mirror will rapidly become fogged over, wet from saliva and water, or dirty from debris. It is necessary to clean the reflective surface of the mirror often so that the dental professional can effectively view the teeth and continue the procedure on the patient. It has therefore been customary for dentists to frequently remove these dental mirrors from the patient's mouth to facilitate cleaning of the reflective surface, and then to reposition the mirror in its original position. This is an unproductive and time-consuming process.

There have been many attempts over the years to make this process easier. For example: U.S. Pat. No. 8,133,052 to Emmons, III (2012); U.S. Pat. No. 5,654,824 to Tarr et al. (1997); U.S. Pat. No. 7,331,785 to Croop et al. (2008); U.S. Pat. No. 3,696,824 to Widen et al. (1976) all are for various forms of self-cleaning dental mirrors. There are several disadvantages to this approach.

Usually a dental practice has already invested significant money into dental mirrors, and has found a brand that they prefer. Replacing all of the mirrors in a dental practice with self-cleaning models would be costly and inefficient.

Many of these self-cleaning dental mirrors make use of suction and/or air blown on the surface of the mirror, or a wiper that moves on the reflective surface. While this may remove some of the debris and saliva from the mirror, the reflective surface is still not clear enough for adequate visualization of the teeth. Further, the production of such self-cleaning mirrors is costly and complicated.

U.S. Pat. No. 7,325,675 to Halkyard (2008) attempts to clean dental mirrors using a complicated extraoral device. Halkyard proposes a series of absorbent dots soaked in anti-fogging material and enclosed in a foil pouch to clean the dental mirror instead of replacing the dental mirror. There are several disadvantages to this approach.

To begin, the absorbent dots are enclosed inside a packet and not readily available to the dentist when needed. When the dental mirror needs to be cleaned, the dentist must stop, put down their handpiece (dental drill), and reach to where they have placed this packet. The packet must then be opened to expose the absorbent dots, the mirror cleaned, the absorbent dots replaced in the packet, the instruments picked back up, and the procedure can then be resumed. When repeated over and over again during a single dental procedure, this process is cumbersome and tedious.

Additionally, the dots are soaked in an anti-fogging solution, and cannot be used with any other solution or used dry. The dots are available in a single shape and size that is not customizable to a particular practitioner. Further, the dots are not readily available or within easy reach. Therefore, there exists a need in the art for a device that addresses these deficiencies.

An objective of the present invention is to provide a quick, economical, and convenient way to clean a dental mirror.

A further objective of the present invention is to provide a cleaning wipe that can be applied to a variety of surfaces, particularly gloves.

Yet another objective of the present invention is to provide a cleaning wipe that can be customized as to size and shape.

A further objective of the present invention is to provide a thin and flexible cleaning wipe that does not interfere with tactile senses.

Yet another objective of the present invention is to provide a cleaning wipe that can be left dry or used in conjunction with a cleaning agent.

A further objective of the present invention is to provide a cleaning wipe that is disposable.

Yet another objective of the present invention is to provide a cleaning wipe that adheres under wet and dry conditions.

A further objective of the present invention is to provide a cleaning wipe that is easily removed.

These and other objectives will be apparent to one of skill in the art based on the following disclosure, drawings, and claims.

SUMMARY OF THE INVENTION

The self-adhering cleaning wipe has a front having a first side and a second side wherein a portion of the first side is covered with an absorbent material. A back is connected to the front having a first side and a second side wherein a portion of the second side is covered with an adhesive material. The adhesive material is adhered to a surface of a protective glove.

DETAILED DESCRIPTION OF THE PREFERRED EMBODIMENTS

Figure 1:
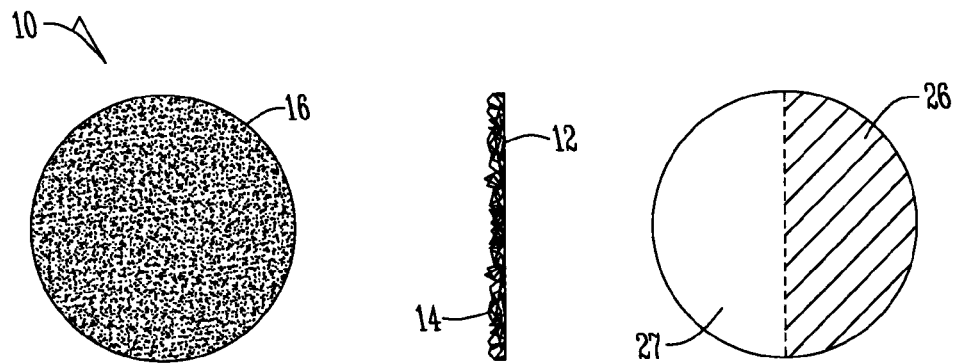
FIG. 1 is a perspective view of the front, back, and side of a self-adhesive cleaning wipe.
Figure 2:
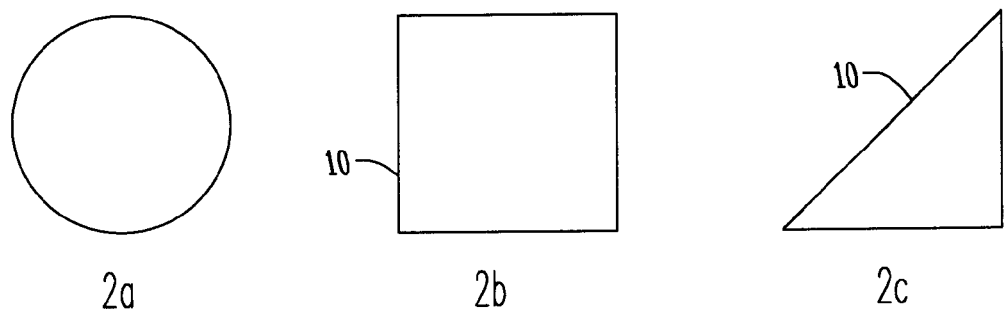
FIG. 2a-2e are various shapes for a self-adhesive cleaning wipe.
Figure 2:
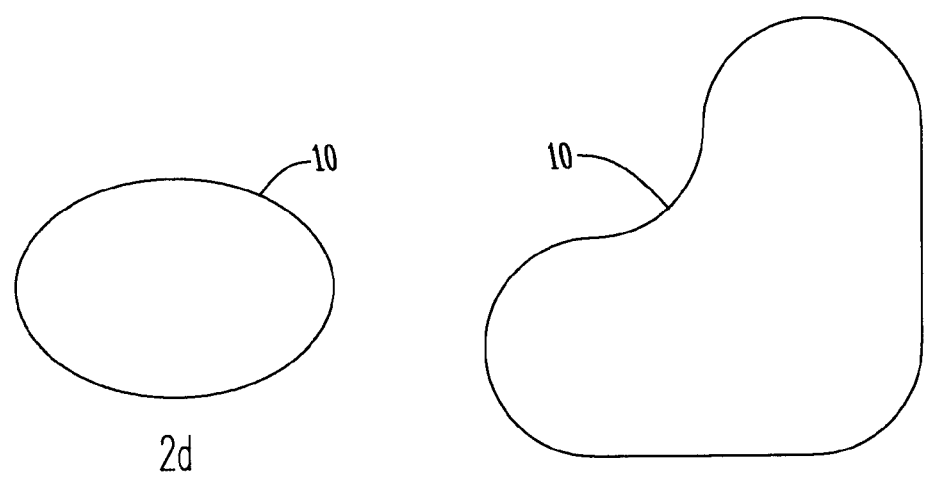
Figure 3:
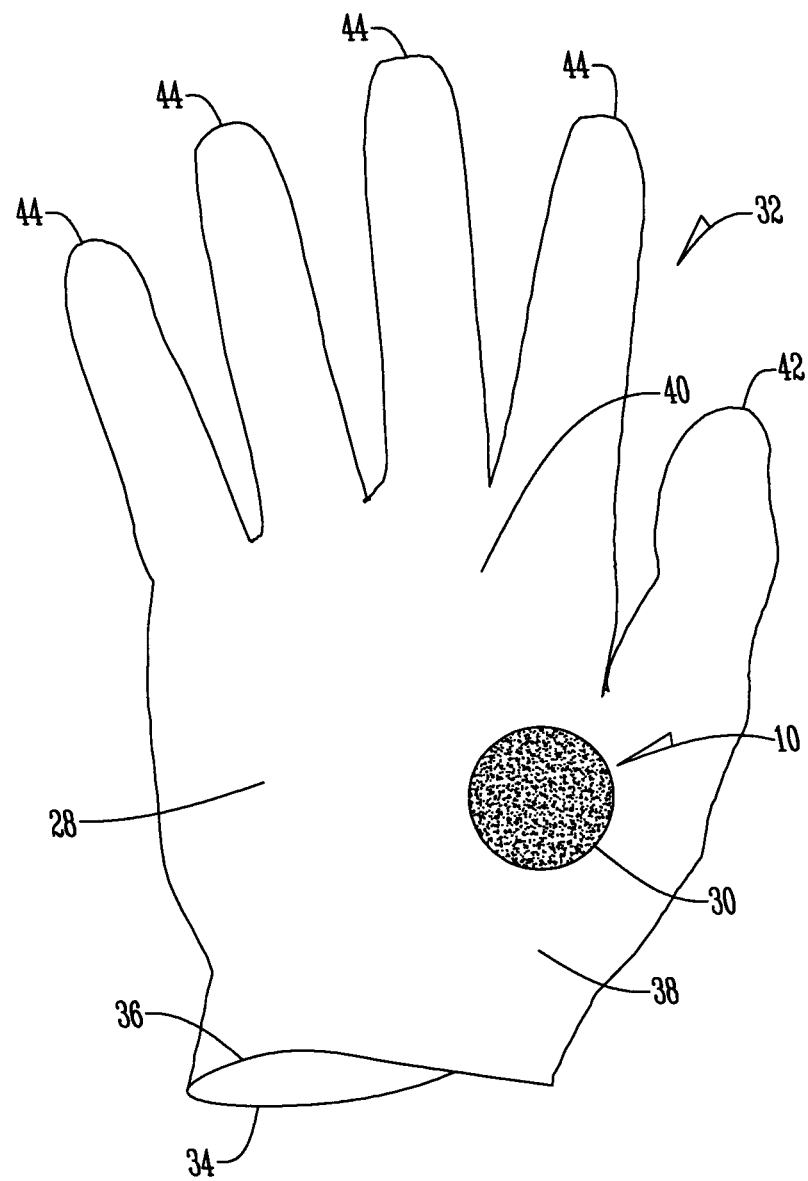
FIG. 3 is a perspective view of a self-adhesive cleaning wipe.

Referring to the Figures, the self-adhesive cleaning wipe 10 has a front 12 connected to a back 14. The cleaning wipe 10 is thin and flexible, so as not to interfere with the tactile sense in the hands and fingers and to be comfortable and easily worn during a procedure. The cleaning wipe 10 is round but may be of any size or shape, as shown in FIG. 2a-2h, including rectangular, triangular, elliptical, or a custom irregular shape. Due to the cleaning wipe 10 being thin the cleaning wipe 10 is easily cut into a custom shape.

The front 12 has a first side 18 and a second side 20. An absorbent material 16 covers the first side 18. The absorbent material 16 can be made of any suitable material such as gauze, felt, or textured cotton material. The back 14 also has a first side 22 and a second side 24. The second side 24 is covered by an adhesive material 26 that allows for adhesion of the cleaning wipe 10 whether it is wet or dry, but allows for easy removal. In another embodiment, the adhesive material 26 covers both the first side 22 and the second side 24 of the back 14. The adhesive material 26 is covered by a removable film 27 that protects the adhesive material 26 from collecting debris.

Figure 4:
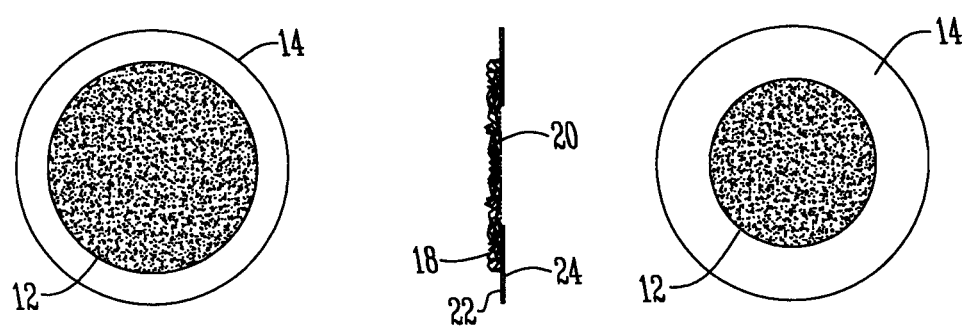
FIG. 4 is a perspective view of the front, back, and side of an alternative embodiment of a self-adhesive cleaning wipe.

In another embodiment the back 14 has a ring shape, as shown in FIG. 4, which extends around the outer border of the front 12 and overlaps a portion of the second side 20 of the front 12 to keep the outer edges of the absorbent material 16 flat to prevent the absorbent material 16 from catching when wiping.

Figure 6:
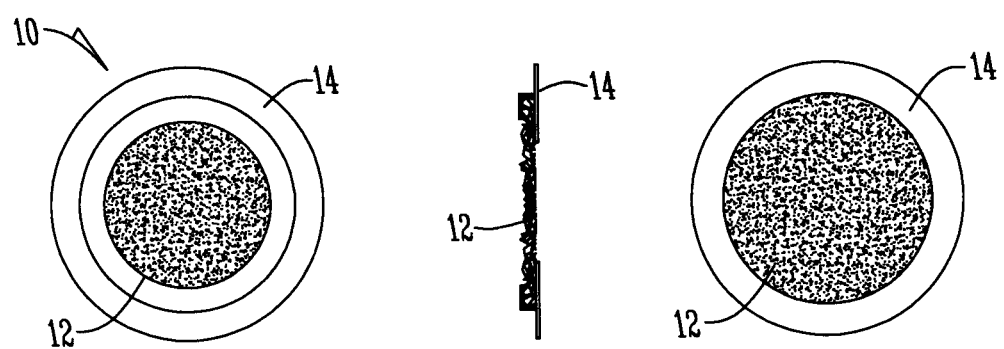
FIG. 6 is a perspective view of the front, back, and side of an alternative embodiment of a self-adhesive cleaning wipe.

In another embodiment, shown in FIG. 6, the back 14 extends around the outer border of the front and overlaps a portion of first side of the front 12 to hold the self-adhesive cleaning wipe 10 securely to the surface 28 on which it is applied.

Figure 5:
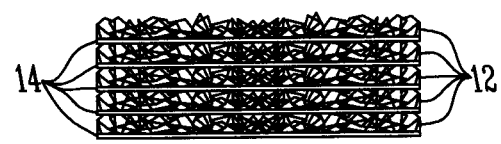
FIG. 5 is a side perspective of self-adhesive cleaning wipes.

In one embodiment, shown in FIG. 5, a cleaning wipe 10 is stacked atop another cleaning wipe 10. This allows the cleaning wipes 10 to be peeled off during a lengthy procedure when the top self-adhesive cleaning wipe 10 becomes saturated with debris. This would easily expose the next cleaning wipe 10 for use.

A cleaning solution 30, such as water, rubbing alcohol, or any other liquid, can be applied to the absorbent material 16 at any time during a procedure.

The surface 28 in one embodiment is a protective glove 32 having a back 34 and a front 36, but can be any convenient surface 28. The glove 32 is a typically a latex glove, but may be made of any material such as nitrile vinyl among others. The front 36 of the glove 32 has a palm section 38, partial palm section 40, a thumb section 42, and a plurality of finger sections 44. The cleaning wipe 10 can be adhered to any section or sections of the glove including the back 34 or the front 36. In particular, the cleaning wipe 10 can be adhered to the palm portion 38, the partial palm portion 40, the thumb portion 42, and/or the plurality of finger sections 44 of the front 36 or back 34. This allows a procedure to continue without interruption of putting down an instrument to clean a mirror.

In operation, a cleaning wipe 10 is selected based on its size and/or shape. Alternatively, the cleaning wipe 10 is cut into a custom shape. Next, the film 27 is removed from the adhesive material 26 of the cleaning wipe 10. The cleaning wipe 10 is then placed on a surface 28 of a protective glove 32 with the adhesive material 26 coming into contact with the surface 28. During an operation the absorbent material 16 is used to clean a mirror or other instrument that is being used. If the cleaning wipe 10 becomes covered with debris or a new patient is seen, the cleaning wipe 10 can be removed and discarded without damaging the protective glove 32. A new cleaning wipe 10 can then be placed on the protective glove 32.

Instead of investing in new equipment, the dentist can continue to use all instrumentation that he/she is used to and simply add the self-adhesive cleaning wipe 10 to what is already being used. This makes the self-adhesive cleaning wipe 10 much more inexpensive and economical than other options currently available.

While the above description contains many specificities, these should not be construed as limitations on the scope of any embodiment, but as exemplifications of various embodiments thereof. Many other ramifications and variations are possible within the teachings of the various embodiments.

For example, a self-adhesive cleaning wipe 10 could be used for other health-care professionals, such as medical doctors, surgeons, etc. for a variety of uses. The cleaning wipes 10 could be affixed conveniently to their protective gloves 32 or other surfaces during medical or surgical procedures to facilitate simple and easy cleaning of instruments. Additionally, the self-adhesive cleaning wipe 10 could be used in industry, automotive, or other fields where someone needs to clean an instrument or tool frequently and efficiently.

Thus the scope should be determined by the appended claims and their legal equivalents, and not by the examples given.

The self-adhesive cleaning wipe 10 will be composed of an absorbent material 16 that is surrounded and/or backed by an adhesive material 26. The self-adhesive cleaning wipe 10 avoids the problems of prior art methods and provides significant advantages over the prior art.

What is claimed is:

1. A cleaning wipe comprising:
   a front having a first side and a second side wherein a portion of the first side is covered with an absorbent material;
   a back connected to the front that overlaps and engages a portion of the absorbent material of the front and having a first side and a second side wherein a portion of the second side of the back is covered with an adhesive material; and
   the adhesive material adhered to a surface of a protective glove.

2. A self-adhesive cleaning wipe comprising:
   an absorbent material having, first and second opposed sides and an outer perimeter, said absorbent material defining a front portion of the wipe;
   a backing material having a central opening and an outer perimeter, an upper surface of the backing material being adhered to the second side of the absorbent material, the central opening of the backing material being spaced radially inward relative to the outer perimeter of the absorbent material and the outer perimeter of the backing material extending radially outward relative to the outer perimeter of the absorbent material, the backing material further including a portion thereof which overlaps and engages substantially the entire periphery of the first side of the absorbent material; and
   a lower surface of the backing material having an adhesive material enabling selective attachment of the wipe to a surface.

3. The self-adhesive cleaning wipe of claim 2 wherein the absorbent material is felt.

4. The self-adhesive cleaning wipe of claim 2 wherein the absorbent material is textured cotton.

5. The self-adhesive cleaning wipe of claim 2 wherein the absorbent material is gauze.

6. The self-adhesive cleaning wipe of claim 2 wherein the cleaning wipe has a circular shape.

7. The self-adhesive cleaning wipe of claim 2 wherein the cleaning wipe has a rectangular shape.

8. The self-ladhesive cleaning wipe of claim 2 wherein the cleaning wipe has a triangular shape.

9. The self-adhesive cleaning wipe of claim 2 wherein the cleaning wipe has an elliptical shape.

10. The self-adhesive cleaning wipe of claim 2 wherein the cleaning wipe has an irregular shape.

11. The self-adhesive cleaning wipe of claim 2 wherein the adhesive material is applied to the totality of the backing material.

12. The self-adhesive cleaning wipe of claim 2 wherein the adhesive material is applied to an outer perimeter of the backing material.

13. The self-adhesive cleaning wipe of claim 2 further comprising a removable film covering the adhesive material.

14. The self-adhesive cleaning, wipe of claim 2 wherein a plurality of cleaning wipes are stacked one on top of another.

\* \* \* \* \*